United States Patent [19]

Isaacson et al.

[11] Patent Number: 5,490,523
[45] Date of Patent: Feb. 13, 1996

[54] FINGER CLIP PULSE OXIMETER

[75] Inventors: Philip O. Isaacson, Chanhassen; David W. Gadtke, Plymouth; Timothy L. Johnson, Medina, all of Minn.

[73] Assignee: Nonin Medical Inc., Plymouth, Minn.

[21] Appl. No.: 268,202

[22] Filed: Jun. 29, 1994

[51] Int. Cl.⁶ ............................................. A61B 5/00
[52] U.S. Cl. ........................................................ 128/633
[58] Field of Search ........................... 128/633, 664–667; 356/39–41

[56] References Cited

U.S. PATENT DOCUMENTS

| | | | |
|---|---|---|---|
| 4,129,124 | 12/1978 | Thalmann | 128/666 |
| 4,353,152 | 10/1982 | O'Connor et al. | 128/666 X |
| 4,394,572 | 7/1983 | Wilber . | |
| 4,446,715 | 5/1984 | Bailey . | |
| 4,621,643 | 11/1986 | New, Jr. et al. . | |
| 4,653,498 | 3/1987 | New, Jr. et al. . | |
| 4,685,464 | 8/1987 | Goldberg et al. | 128/664 X |
| 4,700,708 | 12/1987 | New, Jr. et al. . | |
| 4,765,340 | 8/1988 | Sakai et al. | 128/633 |
| 4,770,179 | 9/1988 | New, Jr. et al. . | |
| 4,773,422 | 9/1988 | Isaacson et al. . | |
| 4,825,872 | 5/1989 | Tan et al. . | |
| 4,825,879 | 5/1989 | Tan et al. . | |
| 4,830,014 | 5/1989 | Goodman et al. . | |
| 4,848,901 | 7/1989 | Hood, Jr. . | |
| 4,865,038 | 9/1989 | Rich et al. . | |
| 4,928,691 | 5/1990 | Nicolson et al. . | |
| 4,964,408 | 10/1990 | Hink et al. . | |
| 4,971,062 | 11/1990 | Hasebe et al. . | |
| 5,035,243 | 7/1991 | Muz . | |
| 5,041,187 | 8/1991 | Hink et al. . | |
| 5,069,213 | 12/1991 | Polezynski . | |
| 5,080,098 | 1/1992 | Willett et al. . | |
| 5,170,786 | 12/1992 | Thomas et al. . | |
| 5,188,108 | 2/1993 | Secker . | |
| 5,209,230 | 5/1993 | Swedlow et al. . | |
| 5,217,012 | 6/1993 | Young et al. . | |
| 5,217,013 | 6/1993 | Lewis et al. | 128/666 X |
| 5,224,478 | 7/1993 | Sakai et al. | 128/666 X |
| 5,237,994 | 8/1993 | Goldberger . | |
| 5,246,003 | 9/1993 | DeLonzor . | |
| 5,247,931 | 9/1993 | Norwood | 128/665 X |
| 5,249,576 | 10/1993 | Goldberger et al. . | |
| 5,279,295 | 1/1994 | Martens et al. . | |
| 5,313,940 | 5/1994 | Fuse et al. | 128/664 X |
| B1 4,446,715 | 9/1991 | Bailey . | |

OTHER PUBLICATIONS

McDermott; "Fitness and Health Care Products Incorporate Advanced Electronics"; Technology News—EDN; Sep. 1980, vol. 25, No. 17, pp. 69–77.

*Primary Examiner*—Angela D. Sykes
*Attorney, Agent, or Firm*—Vidas, Arrett & Steinkraus

[57] ABSTRACT

The invention is directed to Apparatus for measuring a physical parameter, such as the saturation percentage of oxygen in blood. The pulse oximeter is built into the finger clip, and therefore the device is small, lightweight and very portable, as well as more reliable.

11 Claims, 12 Drawing Sheets

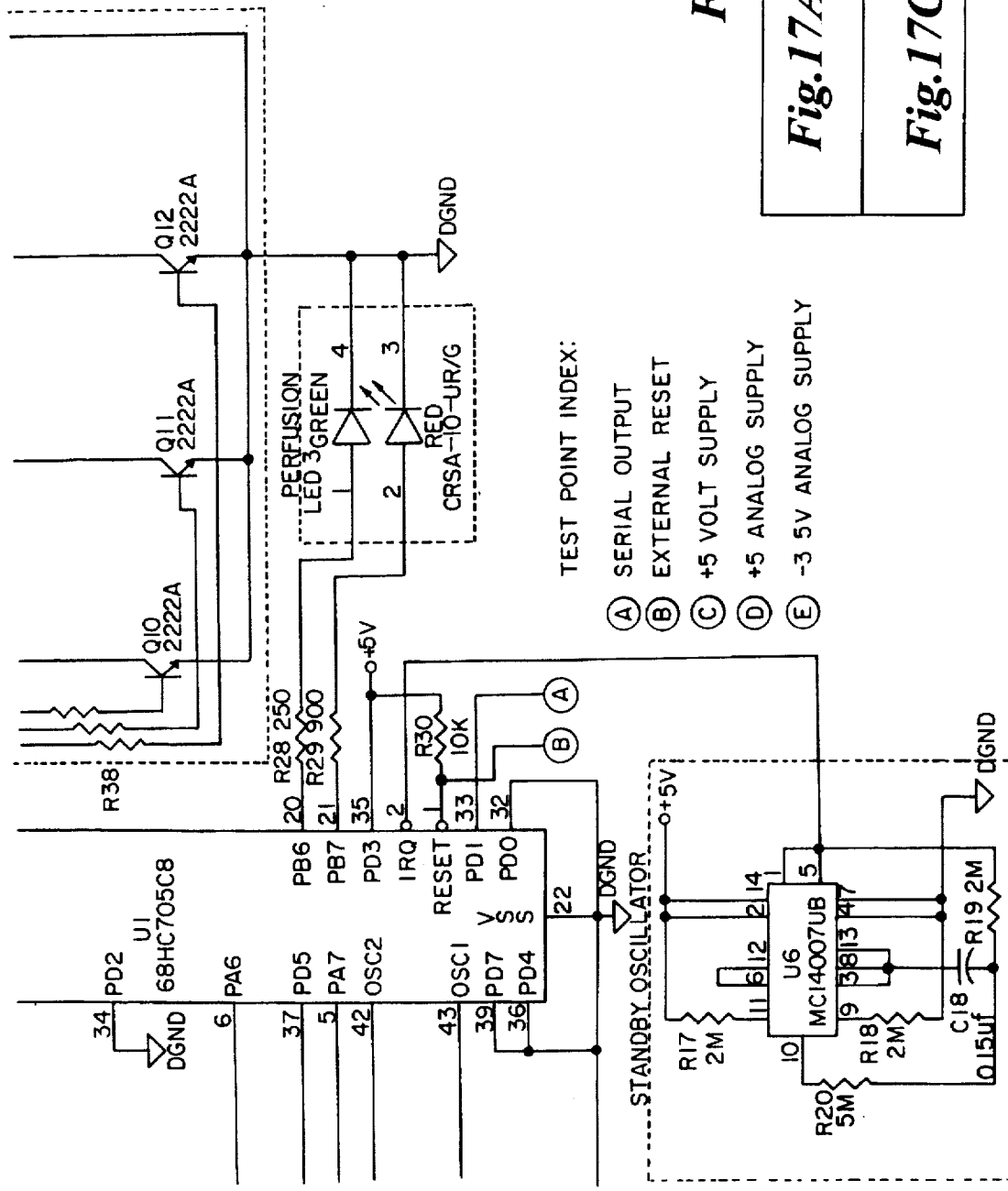

5,490,523

FINGER CLIP PULSE OXIMETER

FIELD OF THE INVENTION

This invention relates generally to medical instrumentation, and more particularly to a finger clip sized pulse oximeter for measuring and indicating the percentage of one or more constituents of arterial blood.

BACKGROUND OF THE INVENTION

Pulse oximetry devices in the past have utilized a sensor, generally attached to the finger, which is conductively coupled to an electronic device which actually measures and indicates the percentage of the desired constituent of arterial blood.

Examples of pulse oximeters using a conductively attached sensor would include U.S. Pat. Nos. 5,279,295; 5,035,243; 5,217,012; 5,249,576; 5,245,003; 5,209,230; 5,170,785; 5,080,098; 5,069,213; 5,041,187; 4,971,052; 4,964,408; 4,928,691; 4,865,038; 4,830,014; 4,825,879; 4,825,872; 4,770,179; 4,700,708; 4,553,498, and 4,621,643.

Applicant also has a patent on a pulse oximeter which utilizes a conductively attached sensor, U.S. Pat. No. 4,773, 422, reissued as RE. 33,543. The entire contents of U.S. Pat. No. 4,773,422, issued Sep. 27, 1988 are hereby incorporated by reference. Applicant's patent pulse oximeter is embodied in several products, including the Model 8600 Portable Pulse Oximeter and the Model 8500 Hand Held Pulse Oximeter.

Despite achieving great commercial success with its line of pulse oximeters, applicant has recognized several problems with existing pulse oximeters, including their own. First, the units are still very bulky and difficult to easily transport from one location to another. These units are typically bought from patient to patient, rather than being in a stationary location. Applicants' units, particularly its hand held model 8500 are often used in connection with ambulances and are moved about a great deal. Secondly, the flexible conductive cable used by all existing pulse oximeters to attach the sensor frequently gets damaged due to being wrapped around the pulse oximeter unit during transport from one location to another. Despite many failsafes built into the cable at either end, over time the cable connections fail.

What is needed is a more portable compact pulse oximeter which eliminates the flexible conductive cable connecting the sensor to the pulse oximeter.

SUMMARY OF THE INVENTION

Applicants' have invented a pulse oximeter which incorporates the electronic processing component and the display into the sensor itself, eliminating the need for a separate component attached to the sensor by a flexible conductive cable. This finger clip pulse oximeter is extremely small, lightweight and durable compared to existing pulse oximeters. It is so small and lightweight that it can be carried around the users neck like a whistle. The inventive finger clip pulse oximeter is battery operated.

The finger clip itself operates like existing finger clips, having an upper and lower portions which are pivotally connected such that as a finger is inserted into the finger clip, the two portions lift apart and pivot to evenly grip the finger. When a finger is inserted into the finger clip pulse oximeter, the device automatically turns fully "on", measures, calculates and displays the measured saturation percentage of $O_2$ ($SpO_2$) on a small display carried on the finger clip.

These and other advantages and features which characterize the invention are pointed out with particularity in the claims annexed hereto and forming a further part hereof. However, for a better understanding of the invention, its advantages and objects obtained by its use, reference should be made to the drawings which form a further part hereof, and the accompanying descriptive matter, in which there is illustrated and described a preferred embodiment of the invention.

BRIEF DESCRIPTION OF THE FIGURES

In the drawings, wherein like reference numerals represent like parts throughout the several views.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 7:
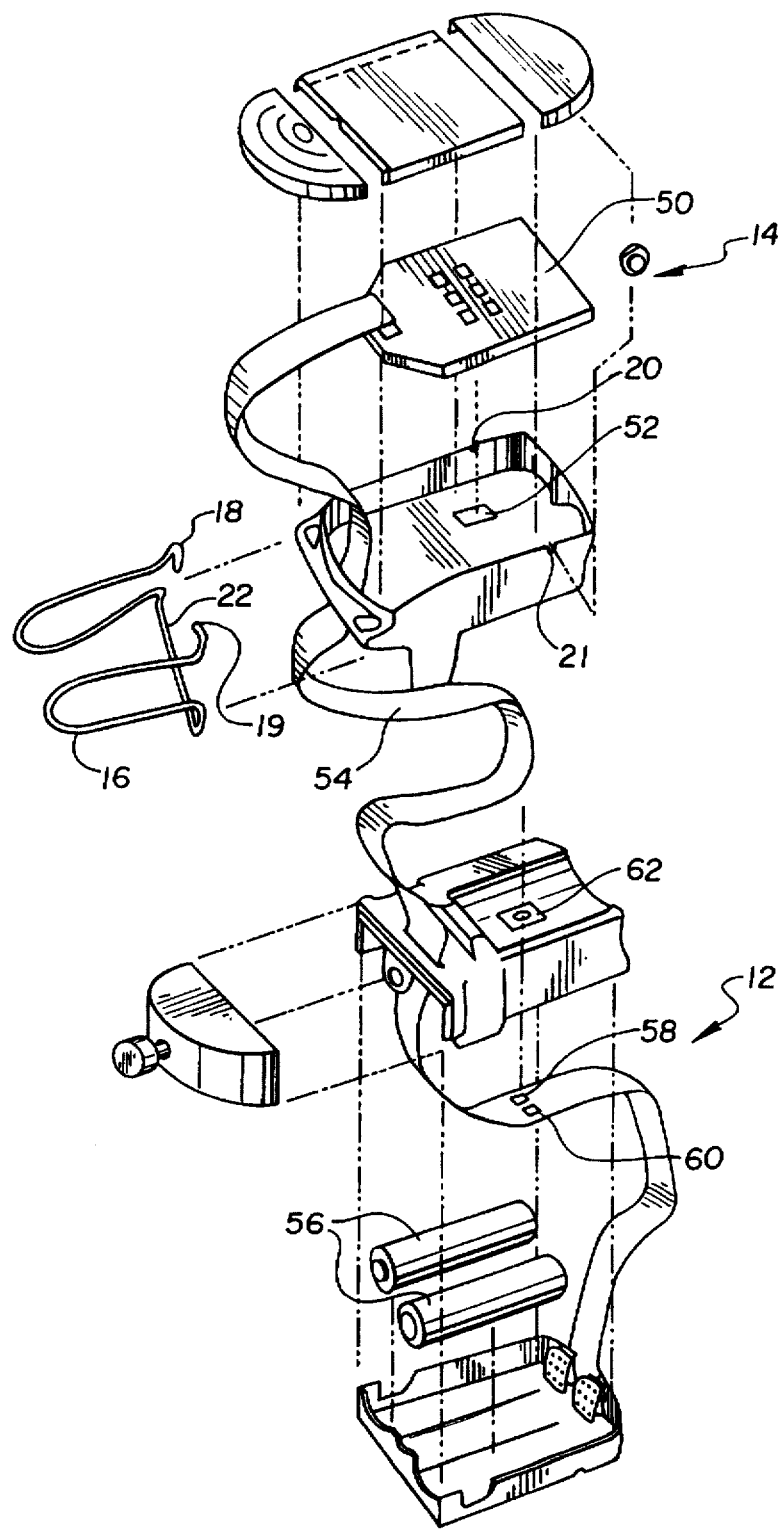
FIG. 7 is an exploded perspective side view of the inventive finger clip.

Referring now to FIGS. 1–4, the preferred embodiment of the finger clip pulse oximeter is shown generally at 10. Finger clip pulse oximeter takes the form of first and second housings 12 and 14, which are interconnected with spring 16. Spring 16 has ends 18 and 19 which fit into two holes 20 and 21 on either side of the second housing 14. Spring 16 is comprised of two generally U-shaped spring elements, which are themselves connected in a side by side manner with a short spring element section 22, as is best seen in FIG. 7. As can be seen best in FIGS. 1 and 4, spring element 22 fits into groove 24 of the bottom of the first housing. Housing 12 has indents 26 and 28 which pivotally receive the tabs 30 and 32 of housing 14. Spring 16 allows the two housings 12 and 14 to pivot and/or separate relative to one another. Cord 34 is optionally provided to allow the finger clip pulse oximeter to be hung around the neck of the user.

Figure 1:
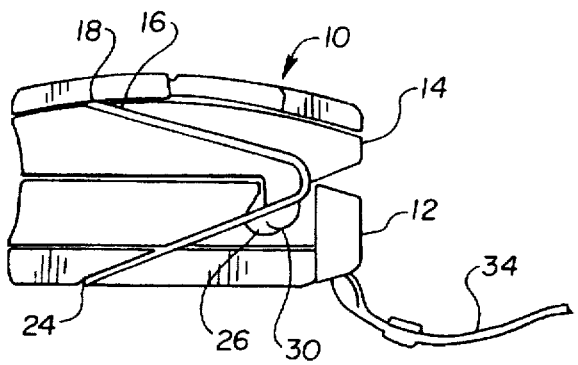
FIG. 1 is a side view of the inventive finger clip pulse oximeter.
Figure 2:
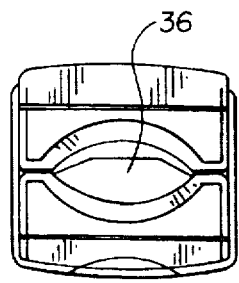
FIG. 2 is a front view of the inventive finger clip pulse oximeter.

FIG. 2 shows opening 36, which is formed by the contours provided in the top of the first housing 12 and the bottom of the second housing 14. Opening 36 receives the inserted finger, and the finger clip pulse oximeter pivots and separates to grippingly receive the finger and position the pulse oximeter 10 for reading the pulse and blood oxygen saturation of the patient.

Figure 3:
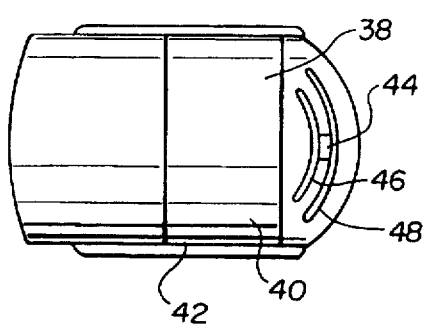
FIG. 3 is a top view of the inventive finger clip pulse oximeter.
Figure 4:
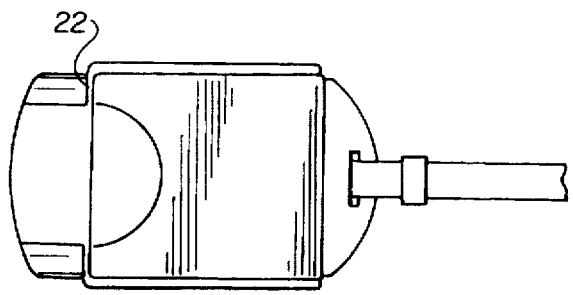
FIG. 4 is a bottom view of the inventive finger clip pulse oximeter.

FIG. 3 shows the top view of the finger clip pulse oximeter 10 in which reference numeral 38 indicates the display which displays the sensed and determined pulse and blood oxygen saturation of the patient ($SpO_2$), each being positioned next to their respective legend 40 and 42. Perfusion indicator 44 is a multicolored LED which flashes green with each pulse amplitude when the reading is within a normal range (percent modulation of infrared light is more than 0.24%), flashes red when the pulse amplitude is too small (percent modulation of infrared light is less than approximately 0.08%), and flashes yellow (by turning on both the green and red simultaneously) when the pulse amplitude is marginal. Raised ridges 46 and 48 are provided to better aid in holding the device.

Finger clip pulse oximeter 10 is very portable due to its light weight and small size. The preferred embodiment weighs approximately 2.2 ounces and its dimensions are approximately 1.3 inches wide by 1.3 inches high by 2.2 inches long.

Figure 5:
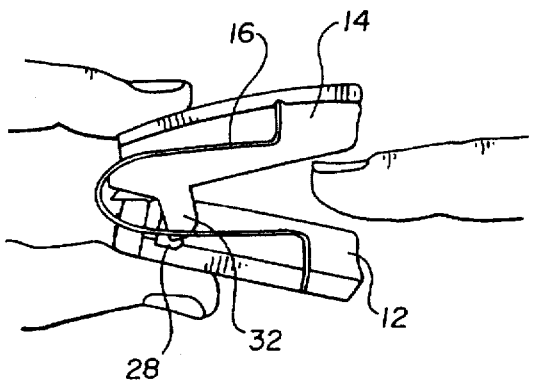
FIG. 5 is a perspective side view showing a finger being inserted into the finger clip.

Referring now to FIGS. 5, finger clip pulse oximeter 10 is shown with the second (or upper) 14 housing pivoted with respect to the first (or lower) housing 12 to enlarge opening 36 to enable insertion of the finger of a patient. Spring 16 provides an urging force which forces the two housings to the closed position shown in FIG. 1.

Figure 6:
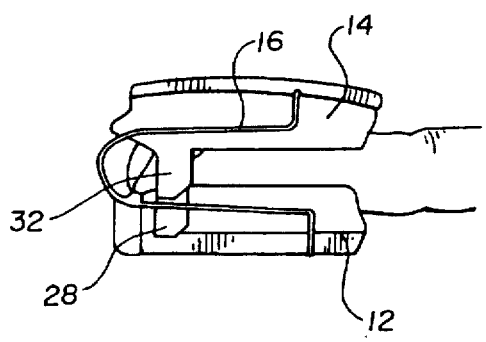
FIG. 6 is a perspective side view of the inventive finger clip showing the finger fully inserted into the finger clip.

Referring now to FIG. 6, after the user releases the finger clip pulse oximeter from the position shown in FIG. 5, the spring 16 causes the two housings 12 and 14 to uniformly grip the inserted finger. Depending on the size of the inserted finger, spring 16 can lift the U-shaped spring end of the second housing, causing the two housings to separate from one another.

Referring now to FIG. 7, an exploded side perspective view of the preferred embodiment of the inventive finger clip pulse oximeter 10 is shown. The upper or second housing is shown generally at 14. Reference numeral 50 is a two sided surface mounted circuit board which contains the electronic circuitry for determining the pulse and blood saturation level; drives the display LED's; drives the radiation emitting LED's; drives the indicator 44 and controls the photodiode which measures the radiation received from the radiation emitting LED's. Circuit board 50 will be discussed in more detail below. Opening 52 in the bottom of the second housing provides access to the radiation emitted by the radiation emitting LED's which is received by the photodiode mounted on the bottom side of the circuit board 50 (discussed further below). Circuit board 50 is electrically connected to the first housing, shown generally at 12 via ribbon cable 54 which allows power and control signals to be sent between the two housings. First housing also holds batteries 56 which are used to power both the two radiation emitting LED's 58 and 60 and circuit board 50. Opening 62 in the top of the first housing allows the radiation emitted by LED's 58 and 60 to be directed towards the photodiode opening 52. In the preferred embodiment, the two openings 52 and 62 are positioned directly opposite each other.

Figure 8:
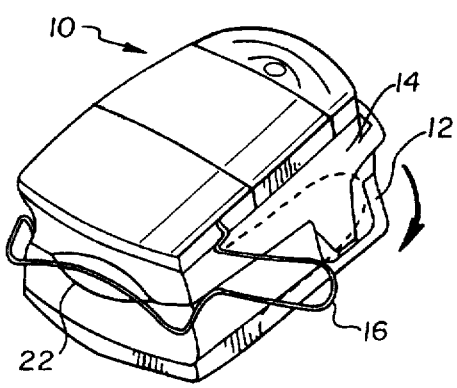
FIG. 8 is a perspective side view showing the spring disengaged from the lower housing
Figure 9:
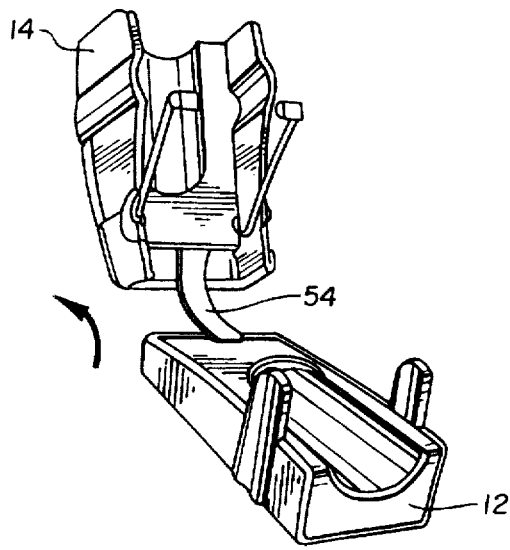
FIG. 9 is a perspective view showing the two housings unconnected from each other.

Referring now to FIG. 8, spring 16 is shown unconnected to the first housing 12. Spring 16 is designed to allow section 22 to be released from the groove in the bottom of the lower section 12, which allows the spring 16 to pivot around ends 18 and 19. As shown best in FIG. 9, the two housings may now be separated for ease of cleaning, since they are only attached via flexible ribbon cable 54.

It should be understood that the location of the various electronic elements in the preferred embodiment is a matter of design choice. For example, the batteries could be located in the second housing, or the circuit board could be located in the first housing. The only important consideration for use with this embodiment (a transmissive type pulse oximeter) is that the photodiode and radiation emitting LED's must be in separate housings.

Figure 10:
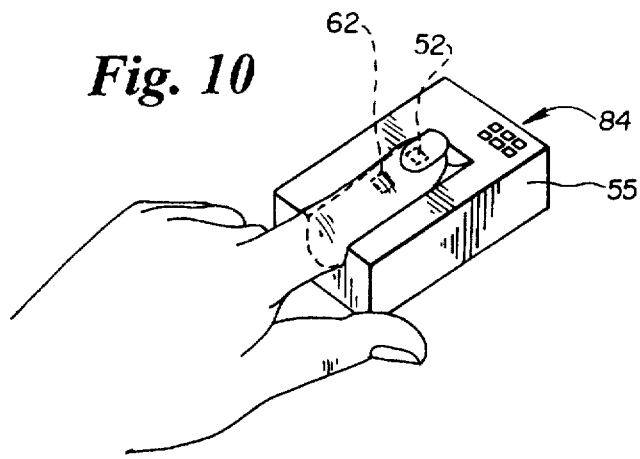
FIG. 10 is an alternative embodiment of the inventive pulse oximeter in which the invention is contained in a single housing, which is contoured to accept a finger pad pressed against the housing.

Referring now to FIG. 10, by utilizing a reflective type pulse oximeter, for example of the type disclosed in U.S. Pat. No. 5,224,478, all of the components can be located in a single housing 55, either the first or second housing, if desired. As is well known in the art, with a reflective type pulse oximeter both the photodiode which receives the radiation and the LED's which emit the radiation are located proximate to each other. FIG. 10 shows an alternate embodiment utilizing a reflective type pulse oximeter, in which the pulse oximeter is housed in a single housing. Rather than using the two housings to act as a finger clip, the user simply presses the pad of their finger against the contoured surface to obtain the reading.

Figure 11:
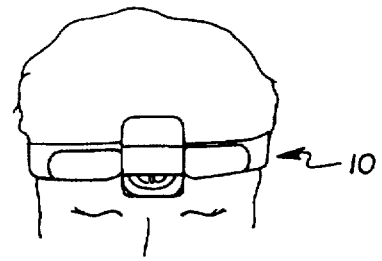
FIG. 11 is a front view showing another alternative embodiment of the inventive pulse oximeter in a single housing contoured for the forehead.
Figure 12:
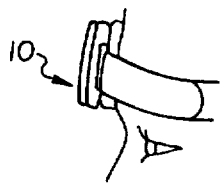
FIG. 12 is a side view of the embodiment of FIG. 11.

Similarly, FIG. 11 and 12 show another alternate embodiment of the pulse oximeter which uses a reflective type pulse oximeter housed in a single housing which is contoured to form fit to the forehead of the patient.

Figure 13:
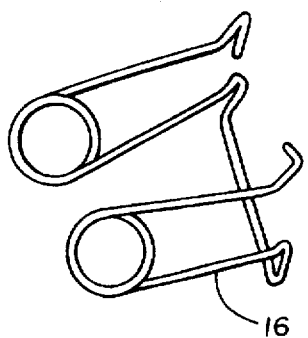
FIG. 13 is an alternative of the spring of the preferred embodiment.

FIG. 13 shows an alternate embodiment of spring 16 which includes an additional loop in the U of the U-shaped spring elements for additional resiliency.

Figure 14:
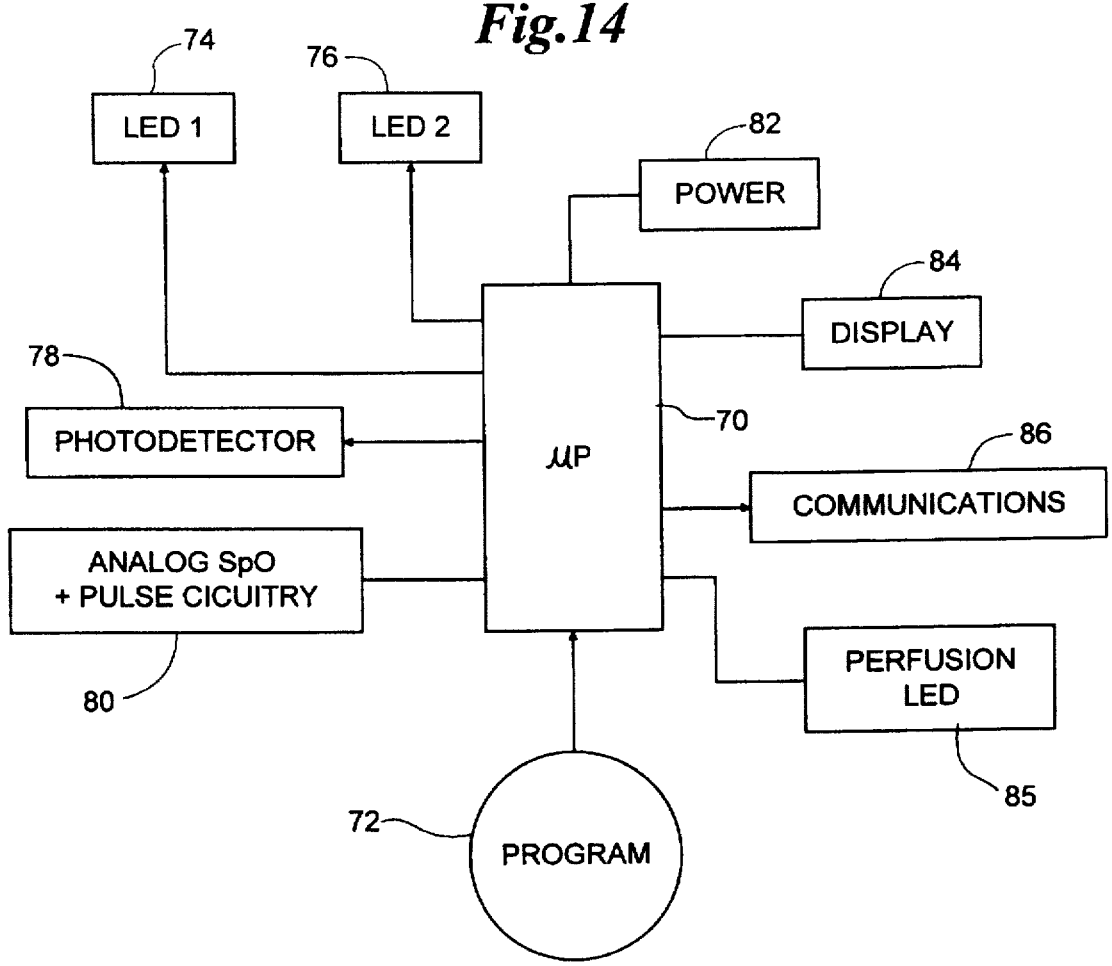
FIG. 14 is a generalized block diagram of the pulse oximeter circuitry.
Figure 15:
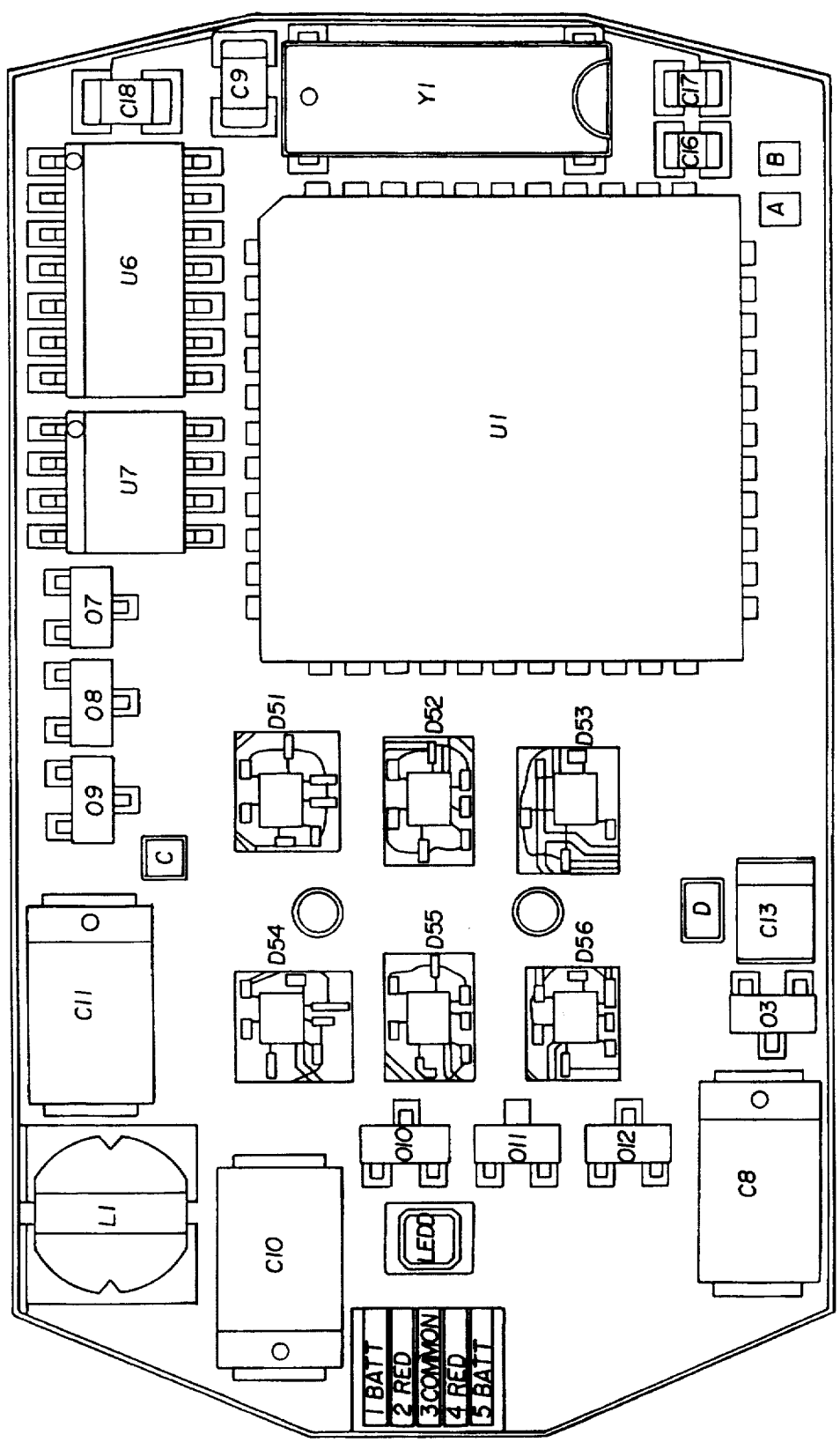
FIG. 15 is a circuit board layout of the top side of the circuit board.
Figure 16:
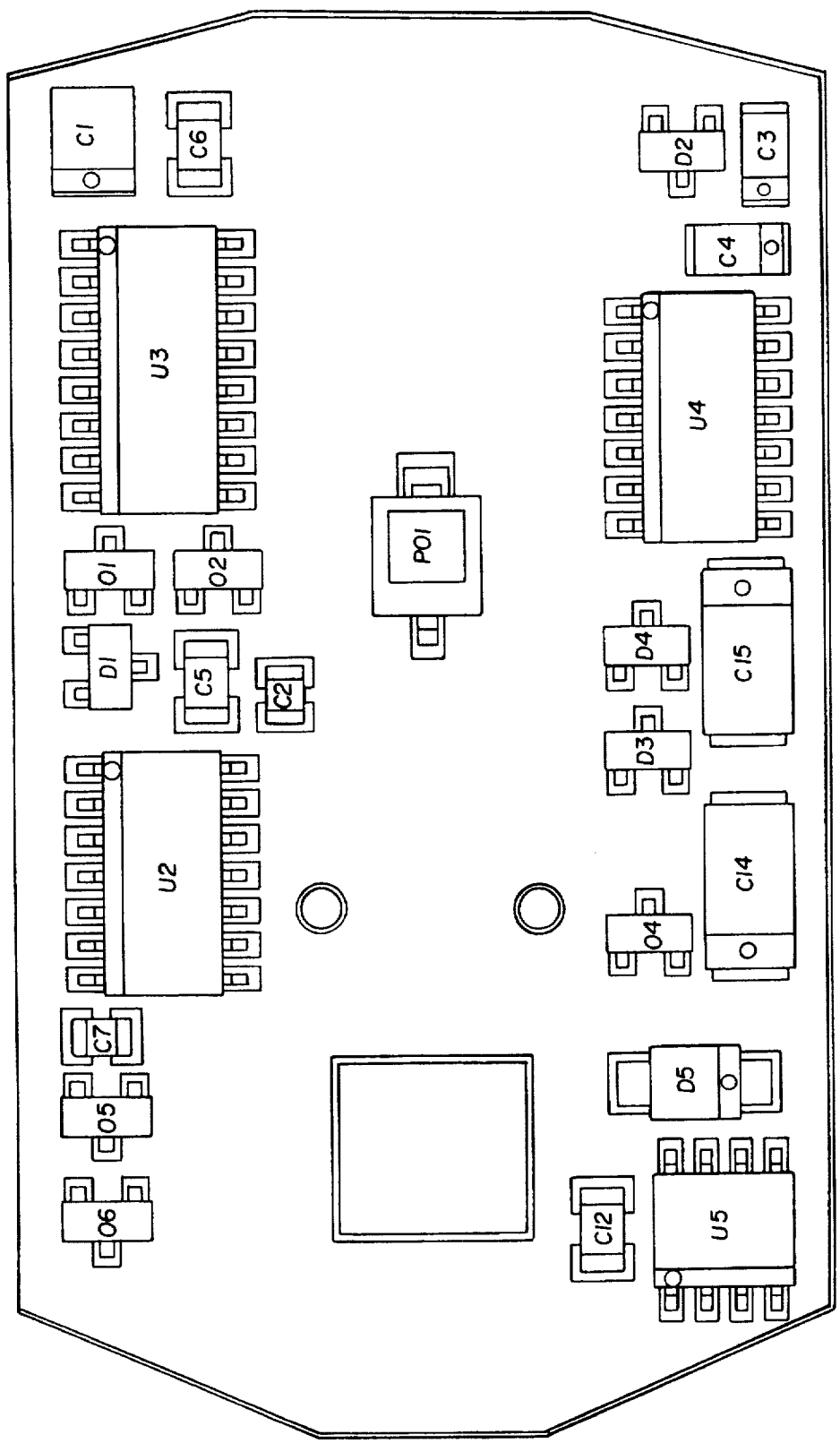
FIG. 16 is a circuit board layout of the bottom side of the circuit board.
Figure 17A:
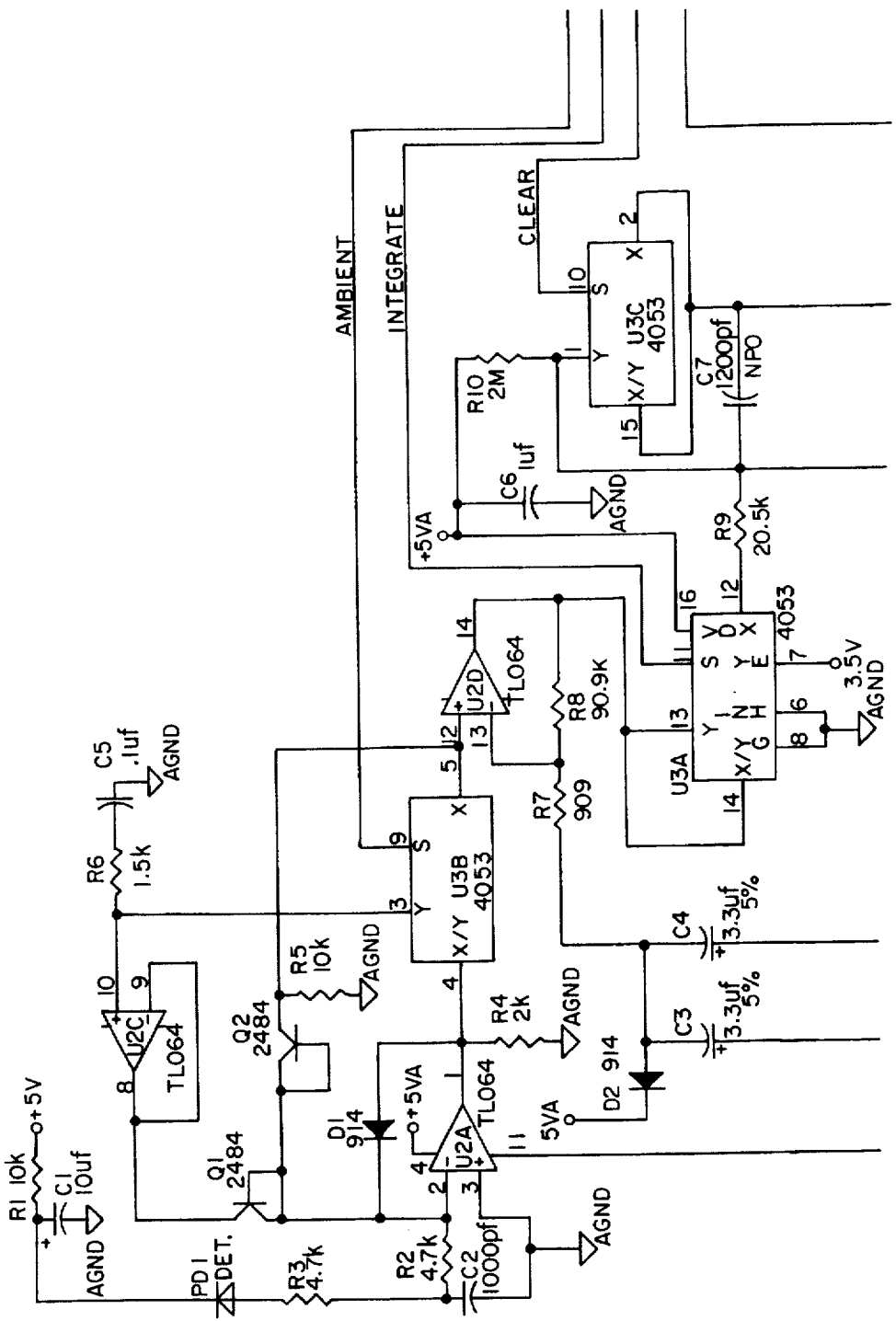
FIG. 17 is a detailed circuit schematic of the pulse oximeter circuitry.
Figure 17B:
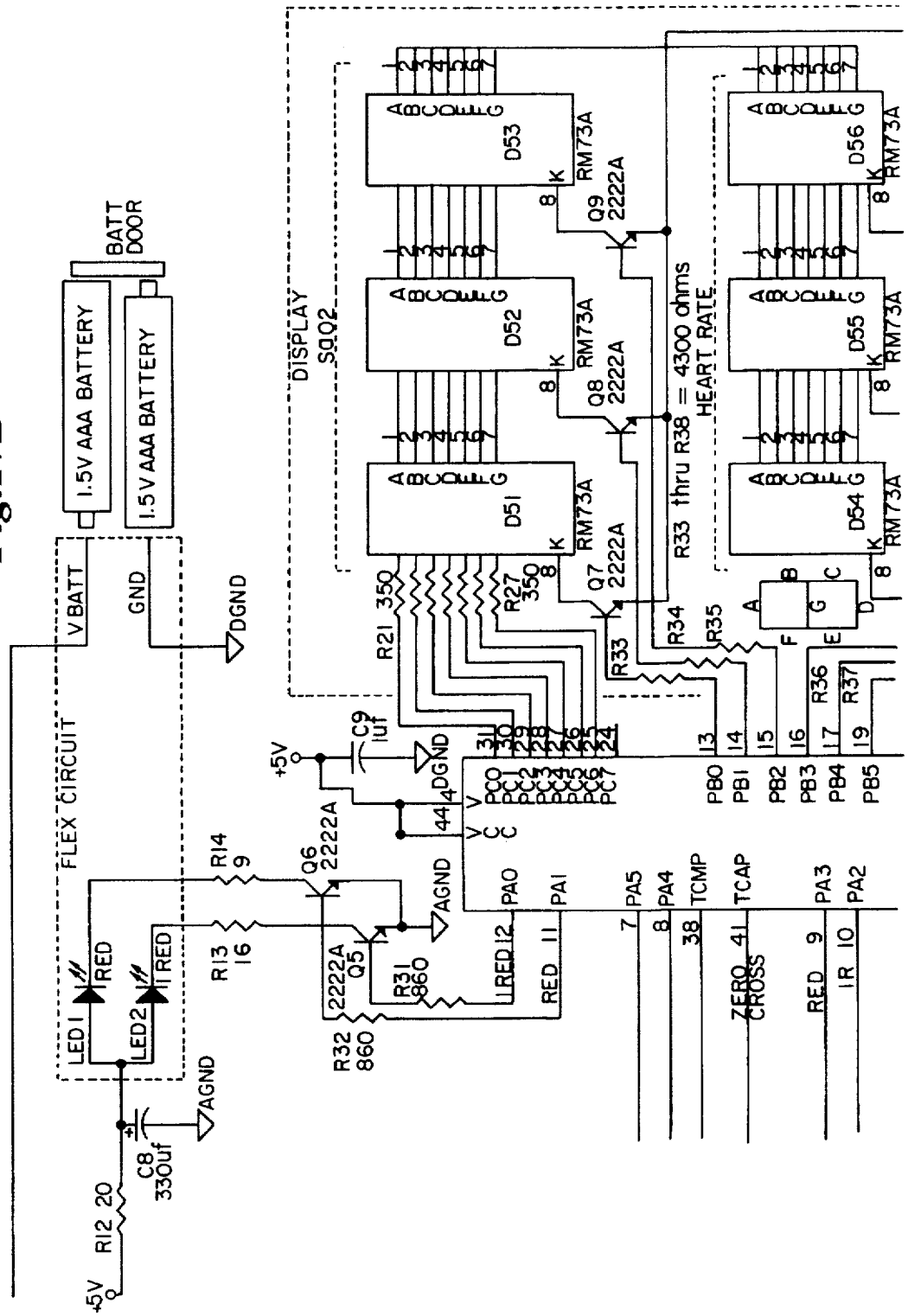
Figure 17C:
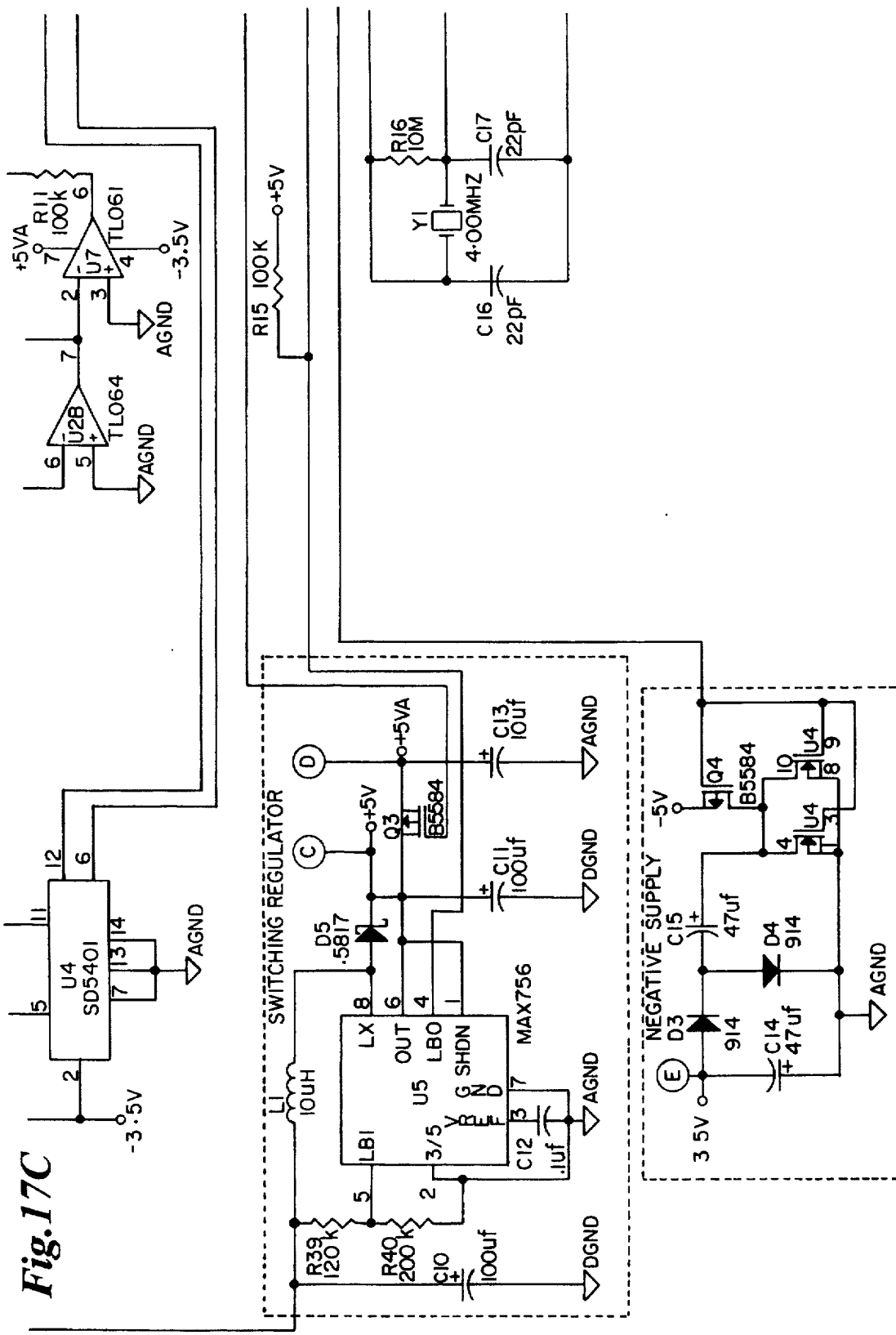

Referring now to FIGS. 14 through 17, the electronic circuit board 50 is discussed in greater detail. The electronic circuit board is described generally in connection with the block diagram in FIG. 14. The corresponding circuit board layout, both top and bottom, are shown in FIGS. 15 and 16 and the corresponding detailed schematic diagram is shown in FIG. 17. In lieu of describing the invention's operation relative to the detailed circuitry, the following description will proceed with respect to the generalized block diagram of FIG. 5, with periodic mention, as necessary, to the corresponding FIGS. 15–17.

Figure 18:
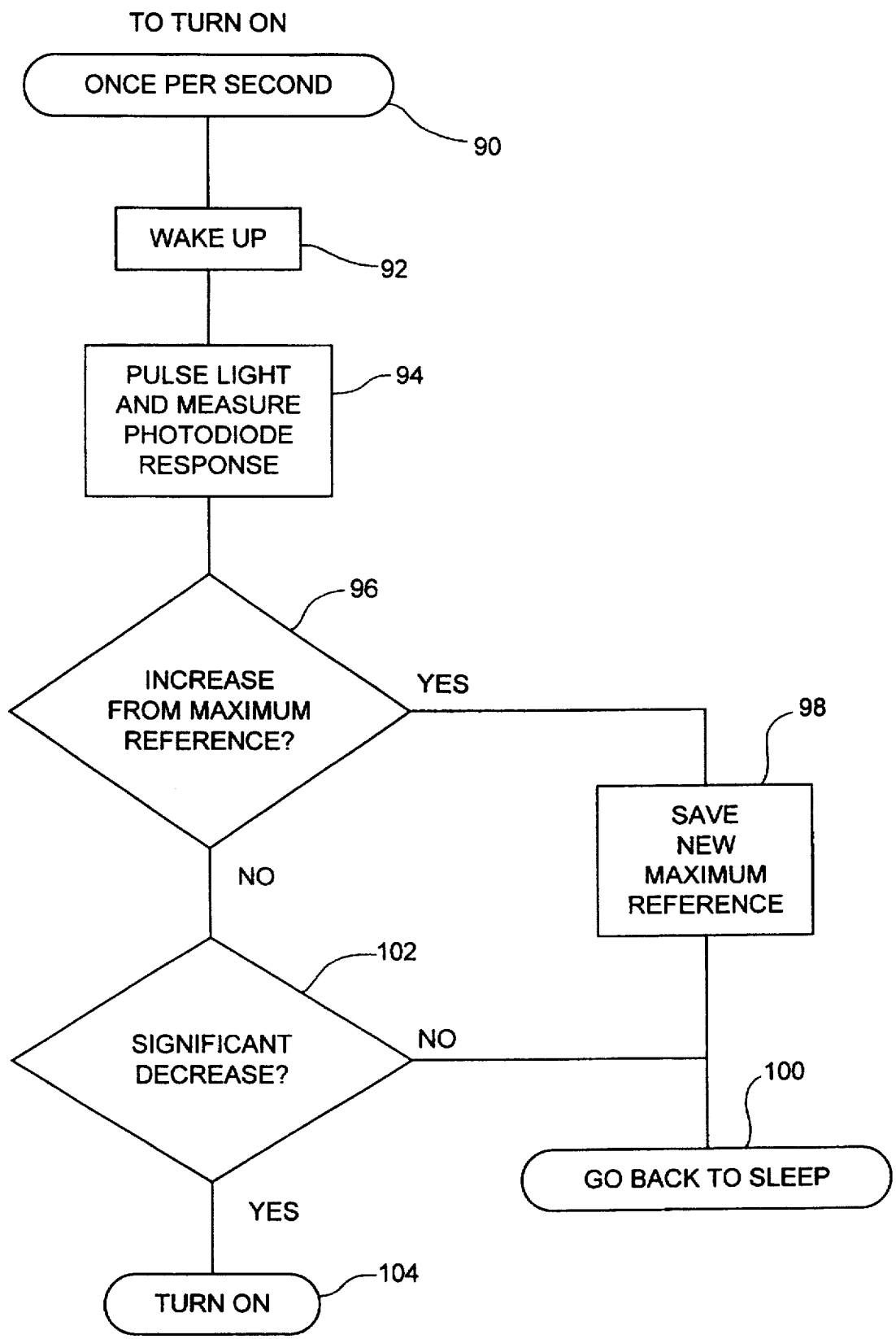
FIG. 18 is a flowchart of the program which monitors photodiode measurements and fully turns "on" the pulse oximeter.
Figure 19:
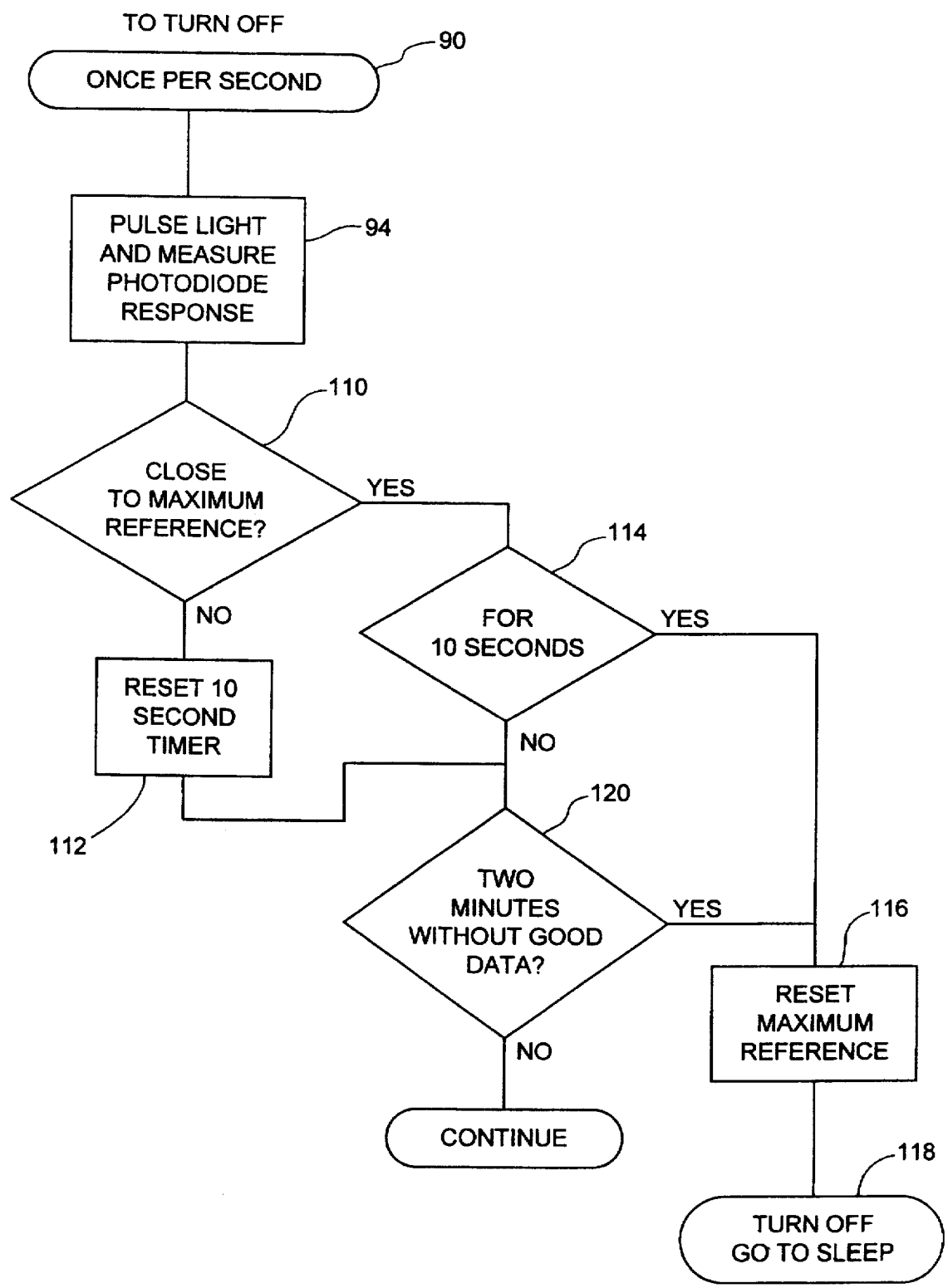
FIG. 19 is a flowchart of the program which turns the pulse oximeter "off".

The microprocessor is shown at block 70 (circuit element U1), which is a single chip microprocessor, a Motorola MC68HC705C8FN in the preferred embodiment, contains its own one time programmable read only memory (OTPROM) and RAM. The programming, shown at reference numeral 72, discussed in FIGS. 18–19 is stored in the OTPROM memory contained inside the single chip microprocessor. The two radiation emitting LED's are shown at blocks 74 and 76 and are controlled by the microprocessor. The photodetector is shown at block 78 (circuit element PD1 in FIG. 16) in FIG. 14. The analog circuitry for conditioning the signal received by the photodetector is at block 80. In the preferred embodiment, the particular apparatus and method of determining the pulse and blood oxygen saturation percentage utilize the technique described in U.S. Pat. No. 4,773,422, reissued as RE. 33,643, which will not be discussed in great detail here. It should be understood that any available technique for determining pulse and blood oxygen saturation percentage can be utilized by the inventive finger clip pulse oximeter.

Power is provided to the microprocessor through the flexible ribbon cable 54, shown at block 82 in FIG. 14. The circuit schematic of FIG. 17 shows six LED's, which make up the display. These six LED's can be seen carried by the top of the circuit board 50. Three of the LED's are used to display the pulse measured and three LED's are used to display the sensed and measured saturation percentage of $O_2$ ($SpO_2$). The display portion of the circuitry is shown at block 84 of FIG. 14. Block 85 in FIG. 14 represents the circuitry for controlling the perfusion LED (reference numeral 44 in FIG. 3). Finally, block 86 represents commonly available communications circuitry (not shown in FIGS. 15–17) for providing for remote display of the pulse or blood oxygen saturation percentage, either conductively coupled or wirelessly coupled to the remote display.

Referring now to FIG. 18, the flowchart corresponding to the program which monitors the photodiode and turns "on", wakes up or shifts the device from a low power mode to a normal operating power mode is shown. Using this program and the apparatus, the inventive pulse oximeter eliminates the need for an "on" switch. Block 90 represents a predetermined time interval, one second in the preferred embodiment, at which time the device turns fully "on" or "wakes up", shown at 92 sufficiently to emit radiation from one or both of the LED's 58 and 60, represented at block 94. The program measures the photodiode response at 94 and determines at 96 whether the light measurement represents an increase from the maximum measurement reference level, stored by the program. If the evaluation is "yes" then the last measured value replaces the reference level and the device returns to a low power state, shown respectively at 98 and 100. If the evaluation is "no" then the program determines at 102 whether the decrease in light measured is a significant decrease from the previous value measured, which is 40 mV which represents a 5 times decrease in the preferred embodiment. If the decrease is not significant the device returns to a low power state at 100. However, if the decrease is significant, this is an indication that a finger has been inserted, interfering with the radiation emitted by the LED's, and therefore turns the device "on" or shifts it to a normal operating state at 104, which also triggers the pulse and blood oxygen saturation determination and display. Block 102 allows the device to be moved from a lighter area to a darker area without triggering the device to wake up, and thereby waste power.

For the embodiments which utilize the reflective type pulse oximeter, the program would be modified to monitor for a significant increase in light rather than a significant decrease, since no light would be reflected unless a finger or other body part, such as a forehead, where in place.

Referring now to FIG. 19, the flowchart corresponding to the program which monitors the photodiode and turns "off", puts to sleep or shifts the device from a normal operating power mode to a low power mode is shown. Block 90, once per second, is determined by the microprocessor timing. Block 94 is the same as in FIG. 18. In order to determine when to put the device to sleep, the program evaluates the light measured by the photodiode to determine if is within a predetermined threshold value compared to the maximum reference value discussed above, shown at block 110. In the preferred embodiment the threshold value would be 2 times (2X) or 50%. If the measured light is not within the permitted range compared to the maximum the timer (block 90) is reset for 10 seconds, shown at block 112, since this is an indication that the finger, forehead etc. is still in place and the device is still operating. If the measured light is within the permitted range, and remains so for at least 10 seconds, shown at block 114, the maximum reference is reset, shown at block 116, and the device is returned to sleep, turned off, or put in its low power mode at block 118. If the measured light is not within the permitted range for 10 seconds (block 114), this indicates light level fluctuations. The program continues to monitor for two minutes (block 120) and if it does not receive good data during those two minutes, i.e. 10 seconds within the permitted range, the device is put to sleep, otherwise the device continues to measure the light received by the photodiode every second.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. Apparatus for measuring the blood oxygen saturation of arterial blood inside a body portion, comprising:

gripping means for releasably gripping a body portion, wherein the gripping means is comprised of finger gripping means for releasably gripping a finger;

a pulse oximeter means for sensing and determining the blood oxygen saturation of the arterial blood inside the gripped body portion, the pulse oximeter means being completely carried by the gripping means;

a display means for displaying the sensed and determined physical parameter, the display means being attached to the gripping means;

power means for providing power to the pulse oximeter means and the display means; and program means operatively connected to the pulse oximeter means and display means for sensing the presence of a finger and switching the apparatus from a low power state to a normal power state.

2. The apparatus of claim 1 wherein the program means senses the absence of a finger and switches the apparatus from a normal power state to a low power state to conserve power.

3. The apparatus of claim 2 including transmission means for transmitting the determined blood oxygen saturation level to a remote display.

4. The apparatus of claim 3 wherein the transmission to the remote display is wireless.

5. The apparatus of claim 1 wherein the program means switches the apparatus from a normal power state to a low power state after a predetermined time interval to conserve power.

6. Apparatus for measuring the blood oxygen saturation of arterial blood inside a body portion, comprising:

gripping means for releasably gripping a body portion, wherein the gripping means is comprised of finger gripping means for releasably gripping a finger, wherein the finger gripping means comprises:

a first housing;

a second housing; and pivot means interconnecting the first and second housings for allowing the first and second housings to pivot relative to one another to releasably grip a finger inserted between the first and second housings, the pivot means being constructed and arranged to allow the first and second housings to separate from one another, wherein the pivot means urges the two housings towards each other, thereby applying pressure to releasably grip the finger inserted between the first and second housings and wherein the pivot means is a spring means comprised of two generally U-shaped spring elements, each generally U-shaped spring element having an upper end and a lower end, the two lower ends being connected in a side by side manner a predetermined distance apart by an elongate spring element such that the two generally U-shaped spring elements are positioned on either side of the first and second housings and oriented such that the open end of the generally U-shaped spring elements faces in the same direction as the finger receiving ends of the first and second housings, and wherein the upper ends of the spring means are pivotally attached to the sides of the first housing and the elongate spring element is releasably received by a groove in a bottom of the second housing, whereby the first and second housings pivot and separate relative to one another to grippingly receive a finger inserted between the first and second housings, and where the first and second housings may be unconnected from one another for ease of cleaning by releasing the elongate spring element from the groove in the bottom of the second housing, enabling the spring means to pivot around its upper ends;

a pulse oximeter means for sensing and determining the blood oxygen saturation of the arterial blood inside the gripped body portion, the pulse oximeter means being completely carried by the gripping means; and a display means for displaying the sensed and determined physical parameter, the display means being attached to the gripping means.

7. The apparatus of claim 6 wherein each generally U-shaped spring element includes an additional loop to increase the resilience in the spring means.

8. A pulse oximeter, comprising:

a housing having a portion of its outer surface contoured to receive the forehead of a patient pressed against the housing;

pulse oximeter means for sensing and determining the blood oxygen saturation of the arterial blood inside the forehead, the pulse oximeter means carried by the housing and further comprising:

radiation emitting means for directing radiation of at least two discrete wavelengths through the arterial blood inside the forehead;

photosensor means for intercepting radiation reflected by the arterial blood inside the forehead;

computation means for determining the blood oxygen saturation level, connected to the photosensor means;

power means for providing power to the radiation emitting means and a display means, and a display means carried by the housing for displaying the blood oxygen saturation level determined by the pulse oximeter means.

9. A pulse oximeter, comprising:

pulse oximeter means for sensing and determining blood oxygen saturation in the arterial blood in a body portion, the pulse oximeter means being in a normally low power state, and wherein the pulse oximeter means is constructed and arranged for sensing and determining the blood oxygen saturation in the arterial blood of a forehead; and power conservation means operatively connected to the pulse oximeter means for sensing the presence of the body portion and which switches the pulse oximeter from a low power state to a normal power state, whereby the pulse oximeter means senses and determines the blood oxygen saturation in the arterial blood in the body portion.

10. A medical device of the type being housed in first and second housings, each housing being generally rectangular shaped having back, front, top, bottom and side ends and wherein the two housings are connected by a pivot means such that the two housings are stacked one on top of the other, the improvement comprising:

a pivot means wherein the pivot means is a spring means comprised of two generally U-shaped spring elements, each generally U-shaped spring element having an upper end and a lower end, the two lower ends being connected in a side by side manner a predetermined distance apart by an elongate spring element such that the two generally U-shaped spring elements are positioned on either side of the first and second housings and oriented such that the open end of the generally U-shaped spring elements faces towards the front wall of the ends of the first and second housings, and wherein the upper ends of the spring means are pivotally attached to the sides of the first housing and the elongate spring element is releasably received by a groove in the bottom of the second housing, whereby the first and second housings may be unconnected from one another for ease of cleaning by releasing the elongate spring element from the groove in the bottom of the second housing, enabling the spring means to pivot around its upper ends.

11. Apparatus for measuring a physical parameter, comprising:

gripping means for releasably gripping a body portion;

electronic means for sensing and determining a physical parameter, carried by the gripping means;

power means for providing power to the electronic means, and non-mechanical automatic on/off means operatively connected to the electronic means which non-mechanically senses the presence of a body portion gripped by the gripping means and switches the apparatus from a low power state to a normal power state, whereby the apparatus senses and determines the physical parameter.

* * * * *

UNITED STATES PATENT AND TRADEMARK OFFICE
CERTIFICATE OF CORRECTION

PATENT NO. : 5,490,523
DATED : Feb. 13, 1996
INVENTOR(S) : Philip O. Isaacson, et al It is certified that error appears in the above-indentified patent and that said Letters Patent is hereby corrected as shown below:

Col. 1, line 26, delete "33,543" and insert -- 33,643 --

Signed and Sealed this

Twenty-third Day of April, 1996

Attest:

BRUCE LEHMAN

*Attesting Officer*   *Commissioner of Patents and Trademarks*